United States Patent [19]

Messina et al.

[11] Patent Number: 5,488,158
[45] Date of Patent: Jan. 30, 1996

[54] PRODUCTION IN CONTINUOUS OF OXAMIDE FOR THE CATALYTIC OXIDATION OF HCN

[75] Inventors: Giuseppe Messina, Alghero; Giovanni M. Sechi, Ozieri; Silvio De Micheli, Milanese, all of Italy

[73] Assignee: Enichem S.p.A., Milan, Italy

[21] Appl. No.: 386,599

[22] Filed: Feb. 10, 1995

Related U.S. Application Data

[63] Continuation of Ser. No. 62,535, May 18, 1993, abandoned.

[30] Foreign Application Priority Data

May 22, 1992 [IT] Italy ................... MI92A0248

[51] Int. Cl.⁶ .................................................. C07C 231/00
[52] U.S. Cl. ........................................... 564/125; 564/160
[58] Field of Search ........................... 564/125, 127, 564/160; 504/334, 335

[56] References Cited

U.S. PATENT DOCUMENTS

| | | | |
|---|---|---|---|
| 3,937,732 | 2/1976 | Uchida et al. | 564/125 |
| 3,989,753 | 11/1976 | Riemenschneider et al. | 564/125 |
| 4,978,786 | 12/1990 | Messina et al. | 564/160 |

FOREIGN PATENT DOCUMENTS

| | | | |
|---|---|---|---|
| 2219153 | 9/1974 | France. | |
| 2423538 | 11/1975 | Germany. | |
| 2427269 | 12/1975 | Germany. | |
| 1616897 | 12/1990 | U.S.S.R. | 564/125 |

OTHER PUBLICATIONS

Soviet Patent Abstracts, Jan. 22, 1992, Derwent Publications Ltd., AN 91–351568/48, SU–A–1 616 897, Dec. 30, 1990.
Soviet Patent Abstracts, Oct. 7, 1992, Derwent Publications Ltd., AN 92 282991/34, SU–A–1 691 362, Nov. 15, 1991.
Patent Abstracts of Japan, vol. 8, No. 130 (C–229), Jun. 16, 1984, JP–A–59 039 858, Mar. 5, 1984.

*Primary Examiner*—Shailendra Kumar
*Attorney, Agent, or Firm*—Oblon, Spivak, McClelland, Maier, & Neustadt

[57] ABSTRACT

A continuous process for the production of oxamide is based on the catalytic oxidation of hydrogen cyanide with oxygen or air in a strong excess in a solution of copper nitrate in water-acetic acid.

The process is carried out in a vertical tubular reactor, with continuous recycling of part of the suspension of oxamides from the bottom to the top of the reactor.

12 Claims, 3 Drawing Sheets

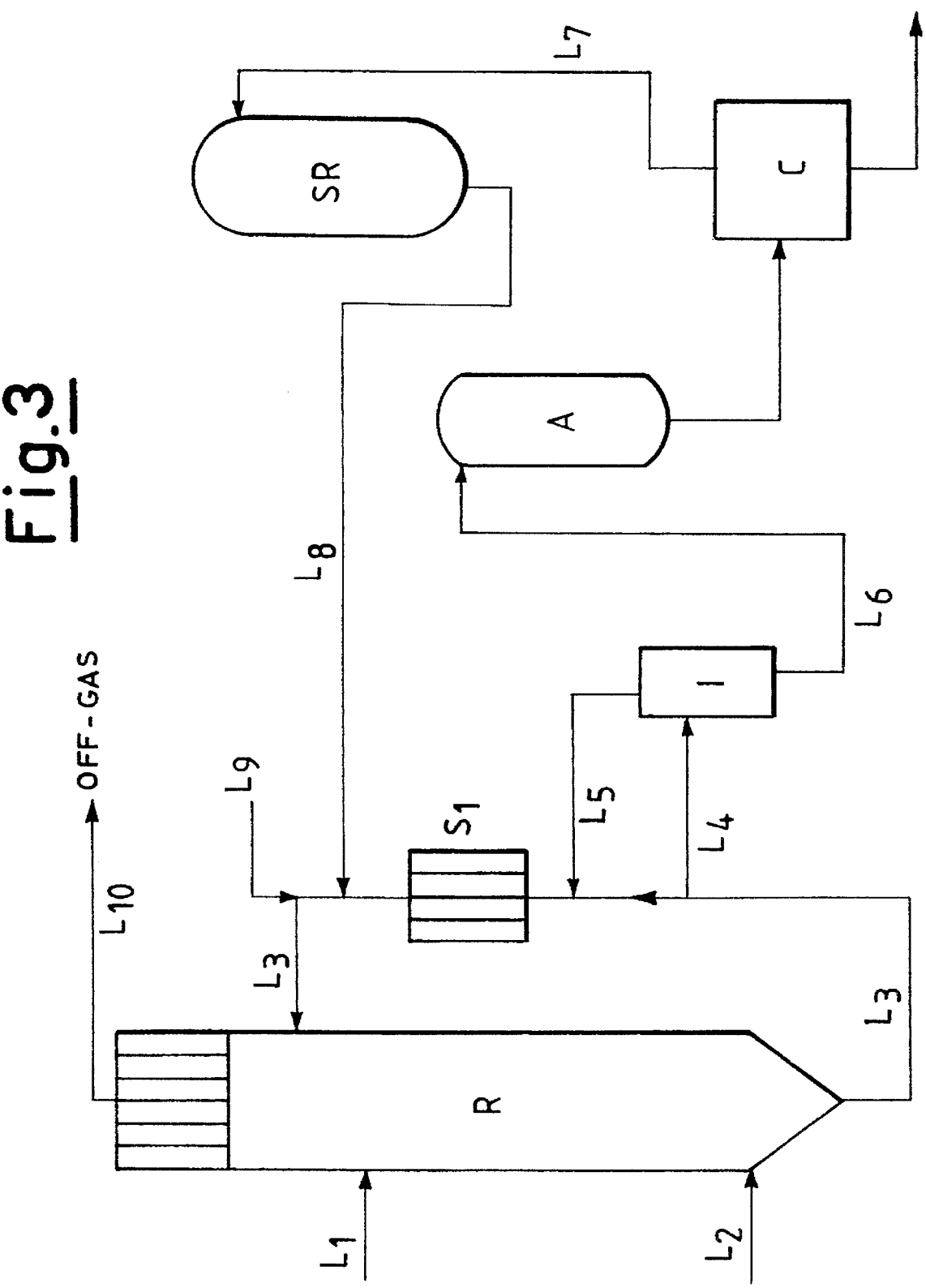

PRODUCTION IN CONTINUOUS OF OXAMIDE FOR THE CATALYTIC OXIDATION OF HCN

This is a Continuation of application Ser. No. 08/062,535, filed on May 18, 1993, now abandoned.

BACKGROUND OF THE INVENTION

1. Field of the Invention

The present invention relates to a procedure for the continuous preparation of oxamide.

2. Discussion of the Background

Oxamide is an organic compound which is used in the synthesis of the widest variety of products ranging from esters, dialkylamides and hydrazides of oxalic acid, to copolyoxamides or copolymers of a bicarboxylic acid with the oxamide of an aliphatic or aromatic diamine; these compounds are described for example in Italian patent applications 20121 A/86, 20274 A/88 and 20276 A/88 filed by the present applicant.

The use of oxamide as a slow release fertilizer is just as well-known [Development in Plant and Soil Sci., 15, Fertilizer Manual, Ed. T. P. Higne; W. Junk Publishers (1985), page 279]; it is based on the slow release of nitrogen by the oxamide.

In spite of the affirmed and increasing use of oxamide, this compound is still not produced on a wide scale because of the relatively high costs and complicated synthesis methods. There are basically three of these methods: the Degussa process (GB 1,251,721), which is based on the oxidation of HCN with hydrogen peroxide, the Sagami process (DE 2034208), which is based on the use of $NO_2$ instead of hydrogen peroxide, and the Hoechst process (DEO 230894, DE 2403120) which is based on the oxidation of HCN with oxygen and air.

Of the three above processes, the first two are rather expensive, both for the type of oxidant used and for the necessity of isolating cyanogen ($N{\equiv}C{-}C{\equiv}N$) as an intermediate product to be hydrolyzed in a subsequent step.

The Hoechst process on the other hand is considered the most accessible and economical of the three, both for the low cost of the oxidant used (oxygen and air), and for the synthesis procedure which consists of a single step; in addition all the products can be recycled, catalyst included.

The catalyst used is an aqueous solution of copper nitrate which is used in the presence of an aliphatic carboxylic acid (acetic acid). A subsequent patent (DE 2402354) emphasizes, in the economy of the process, the role of the oxidant (oxygen or air), which must be advantageously used in great excess with respect to the stoichiometric quantity.

The relative reaction scheme as defined by the authors (W. Riemenschneider, Chemtech., October 1976, pages 658–661) is specified below whereas the scheme of the Hoechst plant is specified in the same article.

$2\ Cu(NO_3)_2 + 4\ HCN \rightarrow (CN)_2 + 2\ CuCN + 4\ HNO_3$ $2\ CuCN + 6\ HNO_3 \rightarrow 2\ Cu(NO_3)_2 + 2\ HCN + 2\ H_2O + 2\ NO_2$ $2\ NO_2 + \frac{1}{2}\ O_2 + H_2O \rightarrow 2\ HNO_3$ $2\ HCN + \frac{1}{2}\ O_2 \rightarrow (CN)_2 + H_2O\ \ (CN)_2 + 2\ H_2O \rightarrow H_2N{-}CO{-}CO{-}NH_2$ $2\ HCN + \frac{1}{2}\ O_2 + H_2O \rightarrow H_2N{-}CO{-}CO{-}NH_2$ The scheme of the reaction zone of the Hoechst process is shown in FIG. 1.

The Hoechst process, as described in the above patents and article, is carried out by continuously feeding in in the lower part of a tubular bubble reactor (T) containing the aqueous acid solution of the catalyst, HCN together with oxygen. The oxamide which is continuously formed precipitates in a crystalline form and is collected at the bottom of the reactor (F), which has a conical shape, in the so-called thickening zone, from which it is transferred as a suspension to a centrifuge, where the oxamide is separated from the catalytic solution which is recycled to the tubular bubble reactor (T); the latter solution is regenerated by adding copper nitrate and the quantity of water consumed according to the stoichiometry of the reaction. The thickening zone of the solid (F) is situated below the inlet of the oxygen and HCN.

In the upper part of the reactor there is an exchanger which cools the off-gases and condenses the vapours of water and acetic acid.

The excess oxygen, hydrogen cyanide and unconverted cyanogen, nitrogen oxides ($N_yO_x$), CO, $CO_2$, $N_2$, deriving from the secondary reactions, leave the head of the tubular reactor together with water and acetic acid.

The results of this process are still not satisfactory however from the point of view of production on an industrial scale because:

there is a heterogeneous distribution of the reagents; in fact the oxygen tends to be distributed preferentially in the upper part of the reactor whereas the hydrogen cyanide, owing to its solubility in the catalyst, tends to move both upwards and downwards with respect to the feeding point, oxygen is never present in the suspension taken from the thickening zone (F) of the reactor whereas the gases contained therein are basically composed of $N_2$, NO, CO and $CO_2$, the recycled catalytic solution always contains reasonable quantities of formamide and acetamide which are destroyed (by oxidation) when re-fed into the reactor as such a quantity does not increase with time.

The presence of NO in the suspension continuously removed from the thickening zone (F) of the reactor, together with the lack of oxygen therein, indicates insufficient re-oxidation of this gas; in fact, in the oxidative process for the formation of oxamide, the nitrates can be reduced to products having a lower oxidation level (NO and $NO_2$) which however, if there is a strong excess of oxygen, as is also recommended in German patent application DE 2402354, should be re-oxidized to nitric acid.

In addition, the lack of oxygen in the thickening zone (F) of the reactor favours the accumulation of reduced products (e.g. $HNO_2$) which can attack the oxamide, oxidizing it exhaustively with the formation of gaseous products such as those specified above, in the suspension at the bottom; for example:

$H_2N{-}CO{-}CO{-}NH_2 + 2HNO_2 \rightarrow 2N_2 + CO + CO_2 + 3H_2O$

The carbon monoxide which is formed according to this reaction, as it is also flammable, increases the concentration of combustible products (hydrogen cyanide, acetic acid, cyanogen) in the gaseous phase and makes more critical the control of the explosivity of the gaseous mixture both in the head of the reactor and in the bubbling-bed.

SUMMARY OF THE INVENTION

The present invention therefore relates to a process for the production of oxamide which, although using the same reagents and same catalytic system of the Hoechst process mentioned above, overcomes the above disadvantages of the known art.

In fact, as mentioned before, the applicant has discovered that the disadvantages of the known art can mainly be attributed to the bad distribution of the reagents and, among these, above all oxygen, both inside the reactor where the synthesis of the oxamide takes place and on the bottom (thickening zone F) and outside the reactor before the oxamide in suspension is separated from the catalytic solution.

In fact, the relatively long period of residence of the oxamide precipitated in the thickening zone (F) of the reactor, before being removed, i.e. in a zone which, as said before, has no oxygen, favours the oxidative destruction of the oxamide as already specified. The same parasitic reaction and also others (formation of formamide and acetamide by the action of acetic acid) occur in the interval between the depositing of the oxamide on the bottom (F) of the reactor, its removal and separation from the solution by centrifugal treatment.

All these disadvantages have been overcome with the synthesis process of oxamide of the applicant.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 3 illustrates an apparatus for carrying out a preferred embodiment of the present process, in which $L_1$ is a line for feeding hydrogen cyanide, $L_2$ is a line for feeding oxygen, $L_3$ is a line for recycling the suspension, $L_4$ is a line for removing the suspension and sending it to a battery of two cyclones, $L_5$ is a line for adding catalyst solution to the recycled suspension, $L_6$ is a line for sending the concentrated suspension of oxamide to the accumulator, $L_7$ is a line for sending the catalyst solution, after separating solid oxamide, to the re-integrating tank, $L_8$ is a line for sending the catalytic solution from the re-integrator tank to the reactor, $L_9$ is a line for re-integrating nitric acid, $L_{10}$ is a line for removing the off gas, R is a reactor, I is a battery of two cyclones, $S_1$ is an exchanger, SR is a re-integrating tank, A is an accumulator, and C is a centrifuge.

In accordance with this, a first aspect of the present invention relates to a process for the continuous preparation of oxamide, by the oxidation of HCN with oxygen or air in the presence of an aqueous solution of copper nitrate $[Cu(NO_3)_2]$ containing acetic acid and nitric acid, basically according to the following scheme:

$$2HCN + \tfrac{1}{2}O_2 + H_2O \rightarrow H_2N\text{—}OC\text{—}CO\text{—}NH_2$$

and including the following operations:
continuous feeding into a tubular vertical reactor:
i) the catalytic solution of copper nitrate $Cu(NO_3)_2$, which also contains acetic acid, nitric acid and the stoichiometric quantity of water consumed in the reaction,
ii) hydrogen cyanide (HCN),
iii) oxygen or air which, bubbling through the tubular reactor, causes the stirring of the suspension of oxamide inside,
continuously removing the suspension of oxamide from the bottom of the tubular reactor and the quantity of oxygen in excess of the stoichiometric quantity from the head of the reactor together with any other gases produced in secondary reactions,
continuously separating the oxamide from a part of the suspension removed from the bottom of the reactor,
recycling the catalyst solution, containing copper nitrate, acetic acid and nitric acid, after adding the stoichiometric quantity of water consumed in the synthesis reaction, this process being characterized in that:
a) the suspension of oxamide is continuously removed from the lowest point of the reactor,
b) a great quantity of the suspension of oxamide removed from the lowest point of the reactor is recycled, re-introducing it into the highest part of the reactor, after cooling it in a heat exchanger at a temperature which is sufficient to maintain the established reaction temperature inside the reactor,
c) an amount of the suspension of oxamide continuously removed from the lowest point of the reactor, is not recycled but is rapidly treated in a battery with two cyclones placed in series, to separate the oxamide from the majority of the acid catalyst solution,
d) the oxygen or air in an excess of 40 to 60% of the stoichiometric quantity is fed to the base of the reactor,
e) the HCN under pressure and in a liquid phase is fed into the highest part of the tubular reactor, at a height which is never less than 4/5 of the height of the aereated liquid inside the column and never more than 8/9 of the same height,
f) the catalytic solution, before being charged into the reactor, is added to the recycled suspension of oxamide, and is then introduced with the same suspension into the upper part of the tubular reactor, and at a height which is never lower than that at which the HCN is introduced.

An important characteristic of the synthesis procedure of oxamide according to the present invention is that the removal, both of the amount of suspension to be recycled and the amount to be separated in the cyclones, is carried out in a single point situated in the lowest part of the reactor.

Figure 1:
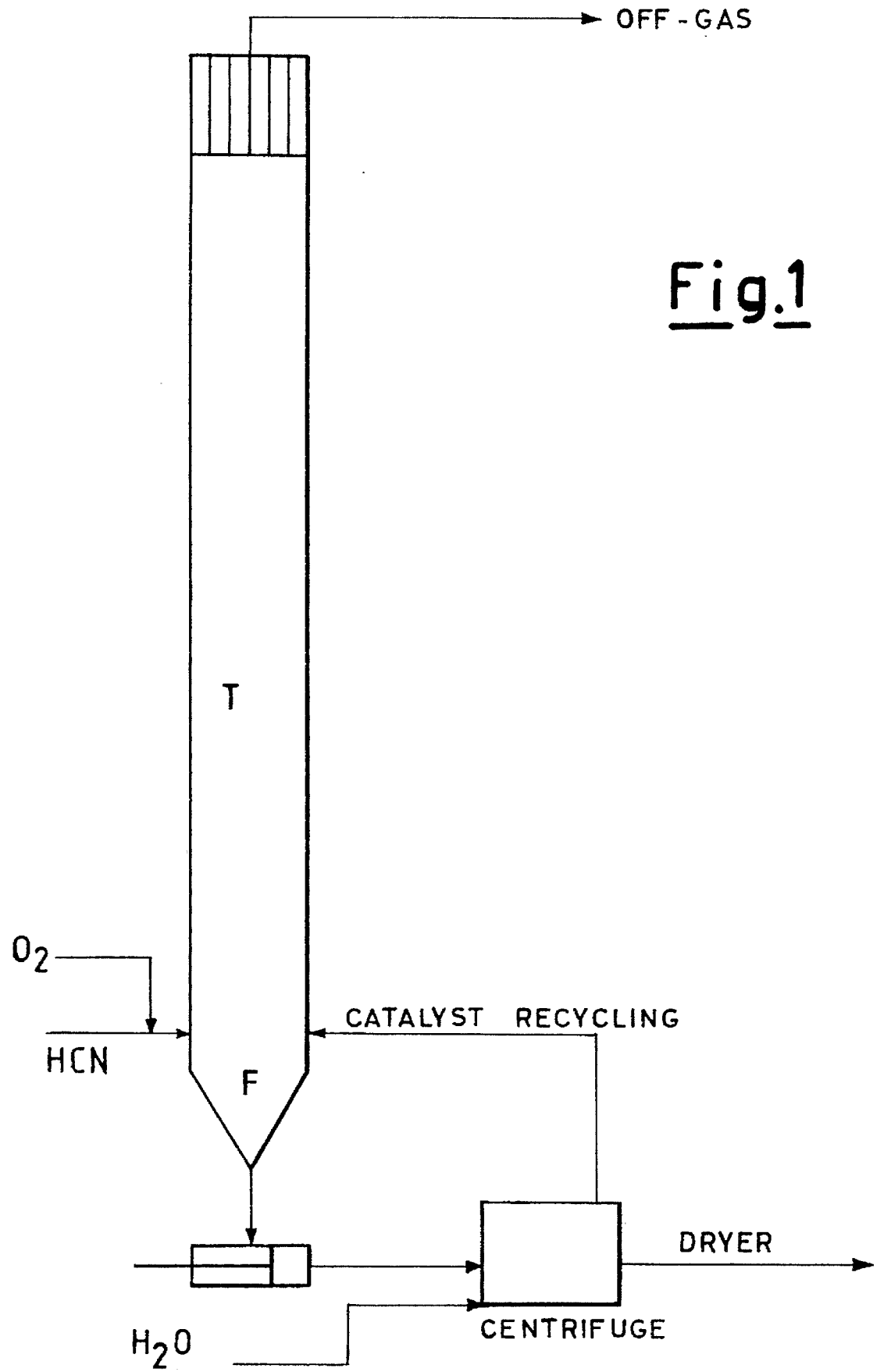
FIG. 1 illustrates a reactor as described in Riemenschneider, *Chemtech*, pp. 658–661, October, 1976, in which: T is a tubular bubble reactor and F is the bottom of the reactor.
Figure 2:
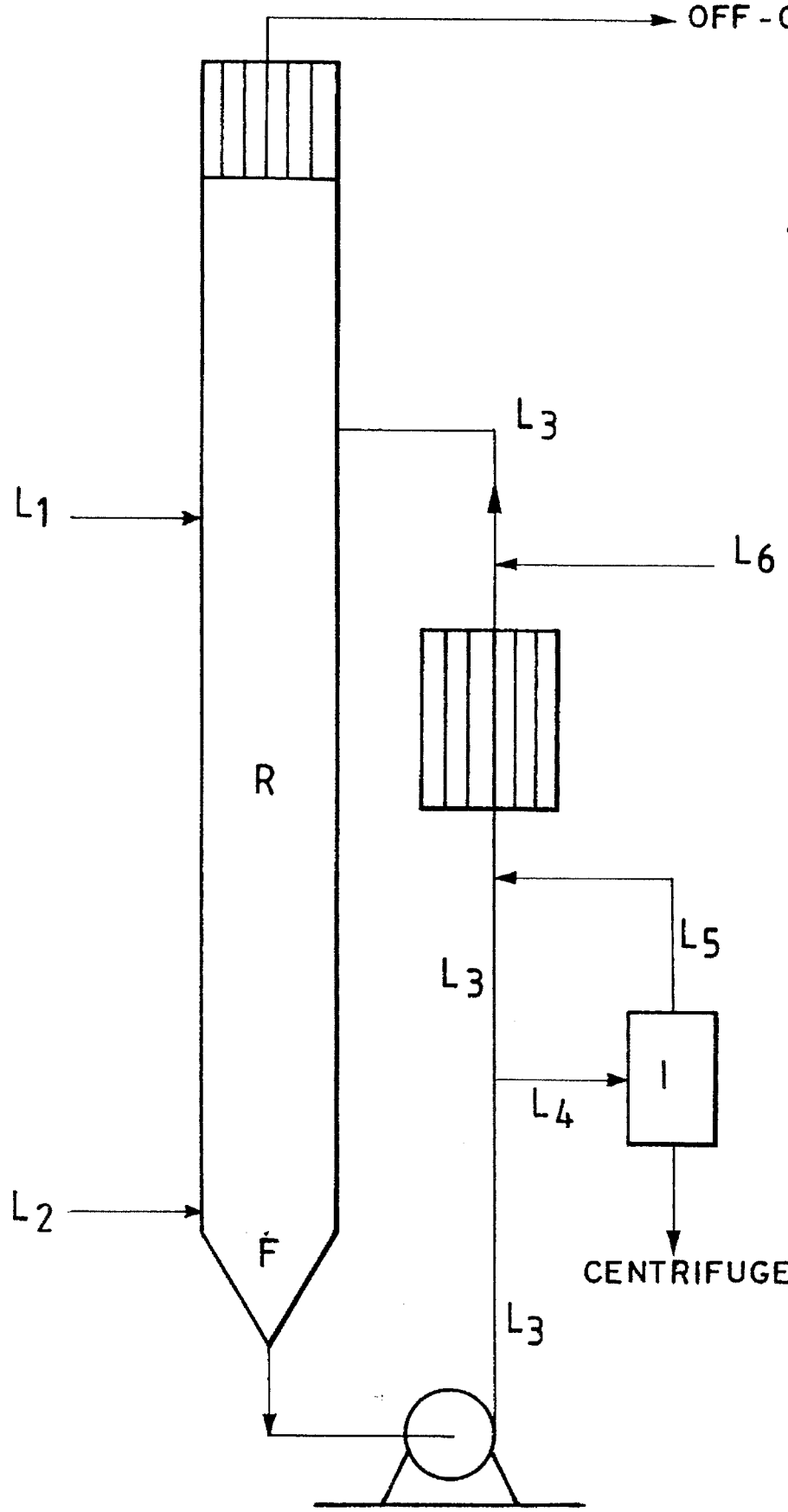
FIG. 2 illustrates a reactor for use in the present process in which: $L_1$ is a line for introducing hydrogen cyanide, $L_2$ is a line for introducing oxygen, $L_3$ is a line for recycling oxamide, $L_4$ is a line for removing the suspension of oxamide, $L_5$ is a line for refeeding the catalytic solution to the productive cycle, $L_6$ is a line for refeeding the catalytic solution to the productive cycle, I is a battery of two cyclones, R is the reactor, and F is the bottom of the reactor.

FIG. 2 shows the scheme of the reaction zone of the synthesis process of oxamide according to the present invention, whereas. FIG. 1, as already specified, shows the scheme of the reaction zone of the synthesis process according to Hoechst.

FIG. 2 clearly shows the reactor (R) from the bottom whereof the suspension of oxamide, most of which is recycled through line $L_3$, is continuously removed; a quantity of the removed suspension is not recycled, but is sent through line $L_4$ to a battery (I) of two cyclones placed in series where the suspension of oxamide is rapidly thickened and sent to the centrifuge; from here, after squeezing the slurry, the catalytic solution is re-fed to the productive cycle through line L$_6$, after being re-integrated with a new aqueous acid solution of copper nitrate; the catalytic solution separated by the thickening treatment effected by the battery with hydrocyclones (I), is, instead, re-fed to the productive cycle through line L$_5$.

FIG. 2 also shows the bottom of the tubular reactor (R) which is narrowed towards the bottom starting from the inlet point of the oxygen which comes from line L$_2$.

Another important characteristic of the present invention lies in the introduction of oxygen and hydrogen cyanide in two separate and clearly distinct points of the reactor; the oxygen, in great excess with respect to the stoichiometric quantity, is admitted to the bottom of the reactor by means of a torus and in the form of small bubbles uniformly distributed on the transversal section of the column of liquid, whereas the HCN is introduced in the upper part of the reactor, in an area situated between 4/5 and 8/5 of the height of the aerated liquid inside the reactor and preferably at 2/3 of the height.

All the above elements guarantee the most uniform distribution possible of oxygen in the reaction mixture and not only inside the reactor but also in the so-called "dead points" (where the oxygen does not bubble) such as the zone in the reactor which is below the feeding point of the oxygen; the volume of this zone, in the synthesis process of the present invention, is infact very small as the two hydrocyclones, which have a negligible volume, replace the thickening zone of the reactor (F in FIG. 1) which, being no longer necessary, has been eliminated.

The two cyclones placed in series and used for the concentration (thickening) of the quantity of suspension of oxamide taken from the recycled amount (through line L$_4$; see FIG. 2), are made by Alfa Laval.

The main operating parameters of the process of the present invention are:

- the concentration of aqueous catalyst solution which contains: from 10 to 15 g/l of copper nitrate and preferably 12.5 g/l; from 3000 to 6000 ppm of HNO$_3$ and from 65% to 70% by weight of acetic acid;
- the total quantity of suspension which is continuously removed from the bottom of the reactor and which is between twice and 6 times the volume of liquid of the reactor per hour; preferably the hourly quantity is 4 times the volume of the reactor;
- the part of suspension taken from the bottom of the reactor which is not recycled but sent to the cyclones for the separation of the oxamide, which is between 25 and 40% in volume; this quantity is preferably 33% of the total volume of suspension taken from the bottom of the reactor;
- the temperature inside the reactor which is between 45° and 65° C. and is preferably 55° C.;
- the pressure in the roof of the reactor, which is between 1 and 2*10$^5$ Pa and preferably (for T=55° C.) 1.5*10$^5$ Pa.

Operating with the synthesis procedure of the present invention conversions of hydrogen cyanide of more than 99.5% are obtained whereas the selectivity to oxamide is higher than 98.5%.

The description of the preferred operating procedure in the synthesis process of oxamide according to the present invention refers to FIG. 3, enclosed with the present description, which shows the operating scheme of the production plant.

The reactor is a vertical reaction column (R), wherein the oxygen forms a bubbling-bed inside the catalytic solution, having a volume of 38.5 m$^3$ and having a ratio between the height of the aerated liquid (catalytic solution) contained therein and the internal diameter of 5.7. The section for the thickening of the solid, which in the Hoechst scheme was situated at the bottom of the reactor, is now separated from the reactor and is composed of the battery with 2 hydrocyclones in series (I), which separates the majority of the catalytic solution from the solid treated suspension.

On the bottom of the reactor, which does not have a thickening zone but is narrowed immediately after the oxygen inlet, a reasonable amount (160 ton/hr) of suspension is continuously removed, the majority of which (107 ton/hr) is recycled, through line L$_3$, in the higher part of the reactor; this is cooled along the way by exchanger S$_1$ to a temperature which is sufficient to maintain a temperature of 55° C. in the reactor; a part of suspension (53 ton/hr) is continuously removed from the recycling line L$_3$ and is sent through L$_4$, as already specified, to the battery with 2 hydrocyclones (I); the catalyst solution which is separated from the suspension (50 ton/hr), is added to the recycled suspension through line L$_5$, whereas the suspension concentrated with oxamide is sent along line L$_6$ to the accumulator (A) and from here to the centrifuge where the solid oxamide is separated from the residuous part of the catalyst solution; the latter is sent, through line L$_7$, to the re-integrating tank SR.

In the re-integrating tank (SR), the solution is restored to the concentration values of copper nitrate (12.5 g/l), water (30%) and acetic acid (70%) existing in the tubular reactor by adding a solution of the three ingredients and is then sent to the reactor by line L$_8$.

The optimum concentration of nitric acid, (4000 ppm) is kept constant by re-integrating it through line L$_9$.

Other parameters used in the synthesis process are: concentration of oxamide in the reactor under standard conditions of about 2.4% by weight; temperature in the tubular reactor of 55° C.; pressure of 1.5*10$^5$ Pa.

The hydrogen cyanide (775 Kg/hr) is fed, in a liquid phase and at a temperature lower than 10° C., into the upper part of the reactor through line L$_1$; the inlet in the reactor is situated at 2/3 of the height of the aerated liquid.

The flow rate of oxygen, which is fed through line L$_2$ into the lower part of the reactor and precisely in the narrowed point of the reactor, is in an excess of 50% with respect to stoichiometric quantity; the excess of oxygen, after being bubbled into the reactor and in countercurrent with respect to the solution of reagents, leaves the head of the reactor and is sent to the incinerator, through line L$_{10}$. With the reactor under steady conditions, and under the operating conditions used, 1250 Kg/hr of oxamide are produced with a conversion of the hydrogen cyanide of 99.8% and selectivity of 99.7%.

We claim:

1. A continuous process for the preparation of oxamide, by the oxidation of HCN with oxygen or air in the presence of an acid aqueous solution of copper nitrate, Cu(NO$_3$)$_2$, according to the following reaction:

$$2HCN + \tfrac{1}{2}O_2 + H_2O \rightarrow H_2N\text{—}OC\text{—}CO\text{—}NH_2,$$

comprising:
  (i) feeding continuously into a vertical tubular reactor, said vertical tubular reactor having a bottom and a head:
   (a) an aqueous catalyst solution comprising acetic acid, nitric acid and copper nitrate Cu(NO$_3$)$_2$,
   (b) hydrogen cyanide, HCN; and
   (c) oxygen or air, to obtain a suspension comprising oxamide;

(ii) continuously removing the suspension of oxamide from the bottom of the tubular reactor and the quantity of oxygen in excess of the stoichiometric quantity from the head of the reactor together with any other gases produced in secondary reactions, (iii) continuously separating said oxamide from a part of the suspension removed from the bottom of the reactor; and (iv) recycling the catalyst solution, comprising copper nitrate, acetic acid and nitric acid, after adding the stoichiometric quantity of water consumed in the synthesis reaction, wherein:

(a) said suspension of oxamide is continuously removed from the lowest point of the reactor;

(b) a quantity of the suspension of oxamide removed from the lowest point of the reactor is recycled, re-introducing it into the highest part of the reactor, after cooling it in a heat exchanger at a temperature which is sufficient to maintain the established reaction temperature inside the reactor;

(c) an amount of the suspension of oxamide continuously removed from the lowest point of the reactor is not recycled but is rapidly treated in a battery with two cyclones placed in series, to separate the oxamide from the majority of the acid catalyst solution;

(d) oxygen or air in an excess of 40 to 60% of the stoichiometric quantity is fed to the base of the reactor, (e) HCN under pressure and in a liquid phase is fed into the highest part of the tubular reactor, at a height which is never less than 4/9 of the height of the aerated liquid inside the column and never more than 8/9 of the same height; and (f) the aqueous catalytic solution, before being charged into the reactor, is added to the recycled suspension of oxamide, and is then introduced with the same suspension into the upper part of the tubular reactor, and at a height which is never lower than that at which said HCN is introduced.

2. The process according to claim 1, wherein said reactor is a vertical column in which the ratio between the height of the liquid suspension and the internal diameter is between the values of 5 and 6.

3. The process according to claim 1, wherein said aqueous catalyst solution comprises from 10 to 15 g/l of copper nitrate; from 3000 to 6000 ppm of nitric acid and from 65 to 70% of acetic acid.

4. The process according to claim 1, wherein the total quantity of suspension which is continuously removed from the bottom of the reactor is between twice and 6 times the volume of the liquid in the reactor for each hour.

5. The process according to claim 1, wherein the total quantity of suspension which is continuously removed form the bottom of the reactor is 4 times the volume of the reactor for each hour.

6. The process according to claim 1, wherein said part of said suspension removed from the reactor which is not recycled but sent to the cyclones for the separation of the oxamide, is between 25 and 40% by volume.

7. The process according to claim 1, wherein the reactor is maintained at a temperature between 45° and 65° C.

8. The process according to claim 1, wherein the reactor is maintained at a pressure between 1 and $2 \times 10^5$ Pa.

9. The process of claim 3, wherein said aqueous catalyst solution comprises 12.5 gl of copper nitrate.

10. The process of claim 6, wherein said part of said suspension removed from the reactor which is not recycled but sent to the cyclones for the separation of the oxamide is 33% by volume.

11. The process of claim 7, wherein said temperature is 55° C.

12. The process of claim 8, wherein said pressure is $1.5 \times 10^5$ Pa at T=55° C.

* * * * *

UNITED STATES PATENT AND TRADEMARK OFFICE
CERTIFICATE OF CORRECTION

PATENT NO. :  5,488,158
DATED      :  Jan. 30, 1996
INVENTOR(S) :  Giuseppe MESSINA, et al.

It is certified that error appears in the above-indentified patent and that said Letters Patent is hereby corrected as shown below:

On the title page, Item [54], the title, should read:

--CONTINUOUS PRODUCTION OF OXAMIDE BY THE CATALYTIC OXIDATION OF HCN--

Item [30], the Foreign Application Priority Data, should read:

--May 22, 1992 [IT] Italy........MI92A001248--

Signed and Sealed this

Second Day of July, 1996

Attest:

BRUCE LEHMAN

Attesting Officer

Commissioner of Patents and Trademarks